United States Patent [19]

Noiles

[11] 3,996,624
[45] Dec. 14, 1976

[54] PROSTHETIC KNEE JOINT

[75] Inventor: Douglas G. Noiles, New Canaan, Conn.

[73] Assignee: United States Surgical Corporation, New York, N.Y.

[22] Filed: Feb. 28, 1975

[21] Appl. No.: 554,144

[52] U.S. Cl. .................................. 3/1.911; 3/1.91; 128/92 C
[51] Int. Cl.² .......................................... A61F 1/24
[58] Field of Search .................... 3/1, 1.9–1.913; 128/92 C, 92 CA

[56] References Cited
UNITED STATES PATENTS

| | | | |
|---|---|---|---|
| 3,765,033 | 10/1973 | Goldberg et al. | 3/1.911 |
| 3,813,700 | 6/1974 | Tavernetti et al. | 3/1.911 |
| 3,837,009 | 9/1974 | Walker | 3/1.911 |

*Primary Examiner*—Ronald L. Frinks
*Attorney, Agent, or Firm*—Fleit & Jacobson

[57] ABSTRACT

A prosthetic knee joint includes a fermoral prosthesis and a tibial prosthesis each having a shank adapted to being fixed to the femur and tibia, respectively. The femoral prosthesis has two laterally spaced apart condyloid elements. The condyloid elements have first bearing surfaces defined by their outer periphery and second bearing surfaces defined by bores in the condyloid elements. The tibial prosthesis has a weight-bearing portion including concave bearing surfaces for supporting the condyloid elements of the femoral prosthesis. The weight-bearing portion of the tibial prosthesis also includes an upstanding arm fitted between the condyloid elements of the femoral prosthesis. A transverse support shaft passes through a hole in the upstanding arm of the tibial prosthesis and is journaled in the bores in the condyloid elements of the femoral prosthesis. The shaft, which is non-rotatably mounted relative to the tibial prosthesis, rotates in the bores in the condyloid elements of the femoral prosthesis while bearing against the second bearing surfaces defined by the bores.

12 Claims, 6 Drawing Figures

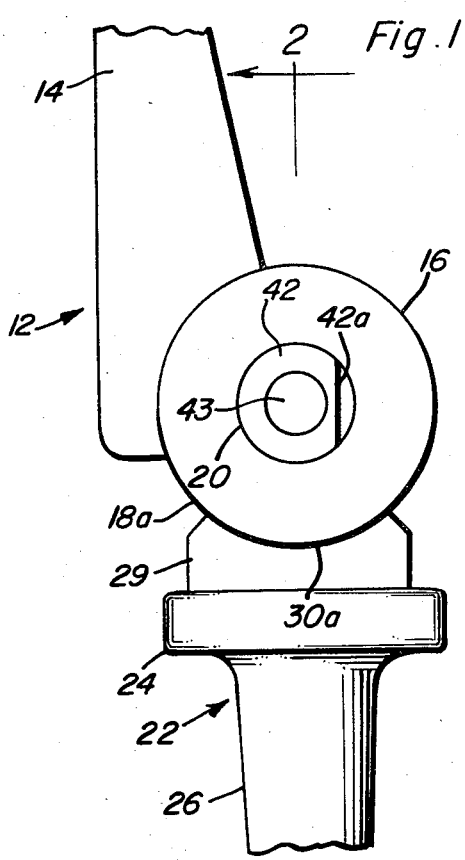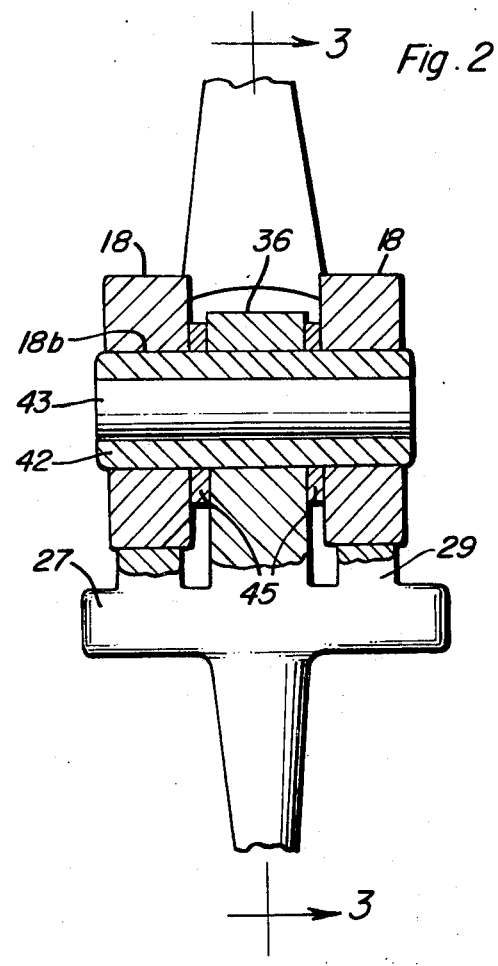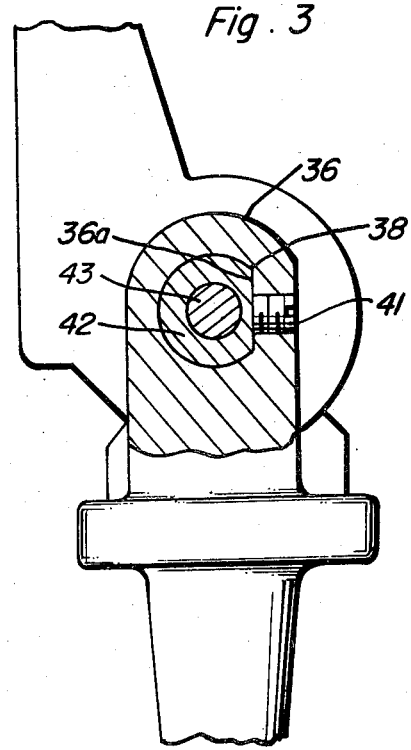

PROSTHETIC KNEE JOINT

BACKGROUND OF THE INVENTION

This invention relates to prosthetic devices, and particularly a prosthetic knee, for providing an articulated joint between bones in the human or animal anatomy.

A prosthetic knee joint conventionally includes a femoral prosthesis having a condyloid portion and a fixation shank. The condyloid portion typically includes laterally spaced apart elements simulating the human knee condyles. In this type of device, the tibial prosthesis includes a weight-bearing portion stimulating the plateau of the tibia of the human knee as well as a fixation shank. The condyloid elements of the femoral prosthesis are supported by non-metallic weight-bearing portions of the tibial prosthesis. A conventional prosthetic knee may also include a shaft between the femoral and tibial prosthesis which is load or weight-bearing. This shaft is normally mounted in non-metallic bearing members non-rotatably mounted relative to the condyloid elements of the femoral prosthesis. As the shaft rotates, the non-metallic bearing members adjacent to the shaft are slowly worn away. At the same time, the non-metallic bearing surfaces of the weight-bearing portion of the tibial prosthesis which support the condyloid elements of the femoral prosthesis are also worn away. This wear results in eccentricity in the initially concentric bearing system, namely, the center of rotation of the condyloid elements deviates from the center of rotation of the shaft. Consequently, the prosthetic knee over a period of time will cease to function properly in that wear will create a distortion in the bearing geometry which will increase local bearing unit loads and thus result in an increased rate of wear, and increased eccentricity.

The device of this invention overcomes the disadvantages of the prior art devices described above by providing a prosthetic device, and particularly a prosthetic knee joint, in which all of the bearing surfaces associated with the femoral prosthesis are on the one single component of the femoral prosthesis so that the normal wear which is associated with these bearing surfaces does not change the relative centers of the rotating surfaces and thereby does not introduce eccentricity in the concentric bearing system. In addition those surfaces associated with the tibial prosthesis which are in loaded moving contact with the four bearing surfaces associated with the femoral prosthesis are of like material in order to have like wearing characteristics. With this arrangement, the prosthetic device will continue to function correctly and to simulate the normal action of the human knee irrespective of wear.

Accordingly, it is an object of this invention to provide an improved prosthetic device such as a prosthetic knee which is capable of functioning smoothly and efficiently under the normal wear involved after implantation.

It is another object of this invention to provide a prosthetic device having a femoral prosthesis defining laterally spaced apart elements simulating the human knee condyles which have first bearing surfaces defined by the outer periphery of the elements and second bearing surfaces defined by openings in the elements which are adapted to receive a weight-bearing shaft.

It is yet another object of this invention to provide a prosthetic device in which the weight-bearing shaft of the prosthesis carries low-friction bearing sleeves which rotate therewith and bear against bearing surfaces defined in the femoral prosthesis.

These and other objects of the invention, as well as many of the attendant advantages thereof, will become more readily apparent when reference is made to the following description taken in conjunction with the accompanying drawings.

SUMMARY OF THE INVENTION

The prosthetic device of this invention includes a femoral prosthesis having a fixation shank for attachment to the femur bone and a condyloid portion including two laterally spaced apart elements which simulate the condyles of the human knee. The two spaced apart condyloid elements each have a first bearing surface defined by the outer periphery of the element and a second bearing surface defined by an opening in the element adapted to receive a support shaft. The tibial prosthesis of the prosthetic device includes a fixation shank for attachment to the tibia bone and a weight-bearing portion having bearing surfaces supporting the first bearing surfaces of the condyloid elements of the femoral prosthesis. The weight-bearing portion of the tibial prosthesis has a center portion fitted between the elements of the femoral prosthesis. A shaft is rotatably mounted in the openings in the condyloid elements of the femoral prosthesis and extends through a hole in the center portion of the tibial prosthesis. The shaft is non-rotatably mounted relative to the tibial prosthesis and the end portions of the shaft are adapted to rotate in the openings of the condyloid elements of the femoral prosthesis while bearing against the second bearing surfaces of the condyloid elements.

BRIEF DESCRIPTION OF THE DRAWINGS

FIG. 1 is an elevational view illustrating one embodiment of this invention;

FIG. 2 is a cross-sectional view taken in the direction of arrows 2—2 in FIG. 1;

FIG. 3 is a cross-sectional view taken in the direction of arrows 3—3 in FIG. 2;

DESCRIPTION OF THE PREFERRED EMBODIMENT

Figure 4:
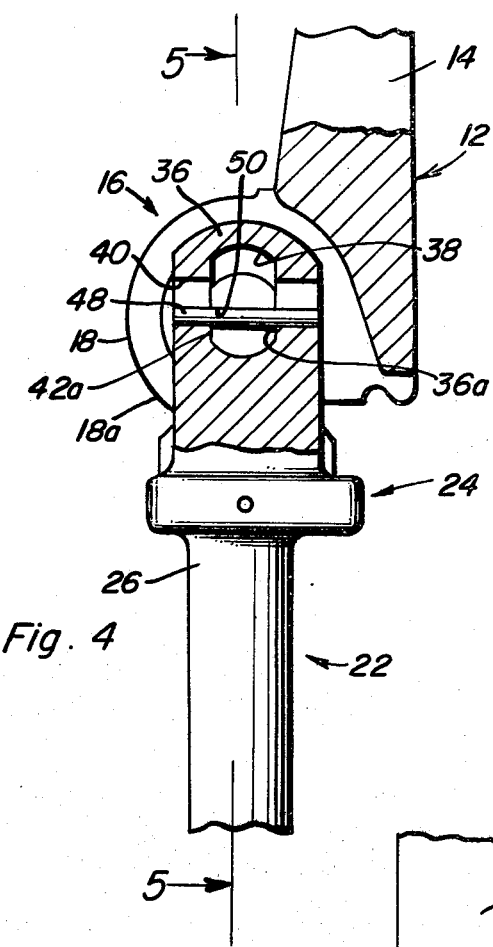
FIG. 4 is a cross-sectional view illustrating a second embodiment of this invention.

With reference to FIGS. 1, 2, and 3, femoral prosthesis 12 includes a shank 14 and a condyloid portion 16. Shank 14 is adapted to be inserted into a cavity formed in the femur (not shown) and joined to the femur in conventional manner such as by cementing. Condylar portion 16 includes two laterally spaced apart condyloid elements 18. Each of condyloid elements 18 has an outer arcuate bearing surface 18a. Bearing surfaces 18a should cover more than one-half of the circumference of condyloid elements 18. Each of condyloid elements 18 has a transverse bore 20 which defines an inner bearing surface 18b. Outer and inner bearing surfaces 18a and 18b, respectively, are concentric and cylindrical as illustrated, but can also be conical, toroidal or any other suitable concentric surfaces of revolution.

Tibial prosthesis 22 includes weight-bearing portion 24 and shank 26. Shank 26 is adapted to be inserted into a cavity formed in the tibia (not shown) and joined to the tibia by cementing or the like. Weight-bearing portion 24 includes a flat plateau portion 27 having two laterally spaced concave bearing members 29 formed thereon. Bearing members 29 have arcuate bearing surfaces 30a which mate with the outer bearing surfaces 18a on condyloid elements 18 of femoral prosthesis 12. Bearing members 29 may be made of a material such as cobaltchromium-molybdenum surgical implant alloy ASTM 75-67 or as ultra high molecular weight polyethylene which wears well and has little frictional resistance. Tibial prosthesis 22 as well as femoral prosthesis 12 are made of stainless steel or a cobaltchromium-molybdenum alloy ASTM 75-67. If bearing members 29 and shaft 42 are non-metallic, tibial prosthesis 22 and femoral prosthesis 12 may be made of titanium alloy ASTM 136-70. Weight-bearing portion 24 of tibial prosthesis 22 also includes an upstanding arm 36 having a transverse hole 38 and set screw 41.

Transverse support shaft 42 has a central portion extending through hole 38 in upstanding arm 36 and end portions received in bores 20 in condyloid elements 18. Shaft 42 is non-rotatably mounted relative to tibial prosthesis 22. As illustrated, shaft 42 has a flat side 42a which abuts against flat side 36a formed by a hole 38 in upstanding arm 36. However, any other suitable means can be provided to insure that tibial prosthesis 22 and shaft 42 have no relative rotation therebetween.

Shaft 42 may be made of surgical implant grade metal or ultra high molecular weight polyethylene. In any case, shaft 42 should be of same material as bearing members 29 so as to have the same wearing characteristics. When shaft 42 is made of a material of low stiffness and strength such as plastic, the shaft may be reinforced by providing metallic or other high strength core 43.

Thrust washers 45 may be mounted on shaft 42 on both sides of member 36 to provide lateral thrust bearing surfaces.

Figure 5:
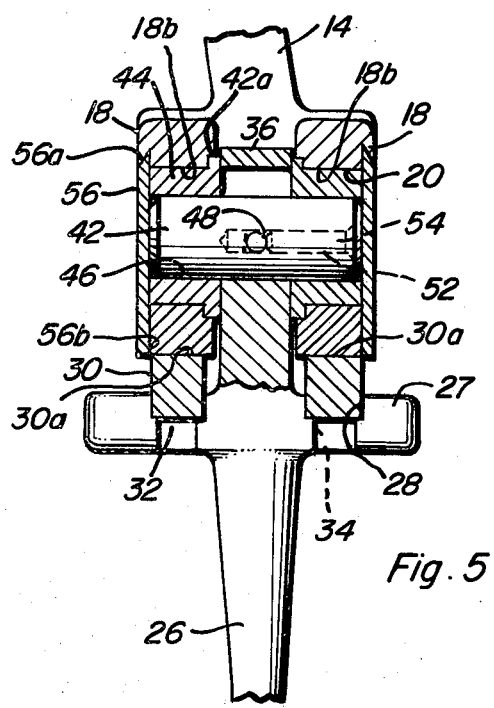
FIG. 5 is a cross-sectional view taken in the direction of arrows 5—5 in FIG. 4.

Referring now to FIGS. 4 and 5, a second embodiment of this invention is illustrated in which like reference numerals refer to like parts. As in the first embodiment, femoral prosthesis 12 includes a shank 14 and a condylar portion 16. Condylar portion 16 includes two laterally spaced apart condyloid elements 18. Each of condyloid elements 18 has an outer arcuate bearing surface 18a. Each of condyloid elements 18 has a transverse bore 20 which defines an inner bearing surface 18b.

Tibial prosthesis 22 includes weight-bearing portion 24 and shank 26. Weight-bearing portion 24 includes a flat plateau portion 27 having two laterally spaced apart slots 28 formed therein. Removably mounted on plateau portion 27 are a pair of bearing blocks 30 which are press-fitted into slots 28. Bearing blocks 30 include downwardly projecting fingers 32 which are received in apertures 34 formed in plateau portion 27. Bearing blocks 30 have arcuate bearing surfaces 30a which mate with the outer bearing surfaces 18a on condyloid elements 18 of femoral prosthesis 12. Bearing blocks 30 are made of a biologically suitable material such as ultra high molecular weight polyethylene which wears well and has little frictional resistance. Weight-bearing portion 24 of tibial prosthesis 22 also includes an upstanding arm 36 having a laterally transverse hole 38 and transverse apertures 40.

Transverse support shaft 42 has a central portion extending through hole 38 in upstanding arm 36 and end portions received in bores 20 in condyloid elements 18. Shaft 42 is non-rotatably mounted relative to tibial prosthesis 22. As illustrated, shaft 42 has flat side walls 42a which abut against flat side walls 36a formed by hole 38 in upstanding arm 36. The end portions of shaft 42 carry bearing sleeves 44. Bearing sleeves 44 have transverse holes 46 for receiving shaft 42 and flanges 42a for preventing transverse movement of the sleeves. Sleeves 44 are fitted freely to rotate in openings 20 in condyloid elements 18 so that flange portions 42a abut upstanding arm 36 on one side and condyloid elements 18 on the other. Sleeves 44 have flat side wall portions 44b defined by bores 46 which abut against flat portions 42a on shaft 42 so that sleeves 44 rotate with shaft 42.

Pin 48 passes through a correspondingly sized aperture 50 in shaft 42 and through apertures 40 in upstanding arm 36. Pin 48 is held in place by screw 52 which is screwed into longitudinally extending threaded aperture 54 in shaft 42. Pin 48 prevents transverse movement of shaft 42 after implantation of the prosthesis. Openings 20 in condyloid elements 18 are closed by end caps 56. End caps 56 have beveled edges 56a and detents 56b which fit into corresponding openings in condyloid elements 18. End caps 56 also prevent transverse movement of shaft 42 after installation so that pin 48 can optionally be deleted if desired. As seen particularly in FIG. 5, hole 38 and apertures 40 in upstanding arm 36 may be elongated in the direction of the femoral prosthesis which is the side of hole 38 which is normally not loaded when the joint is weight-bearing. This clearance can be advantageous to extend the range of extreme flexion of the joint.

Figure 6:
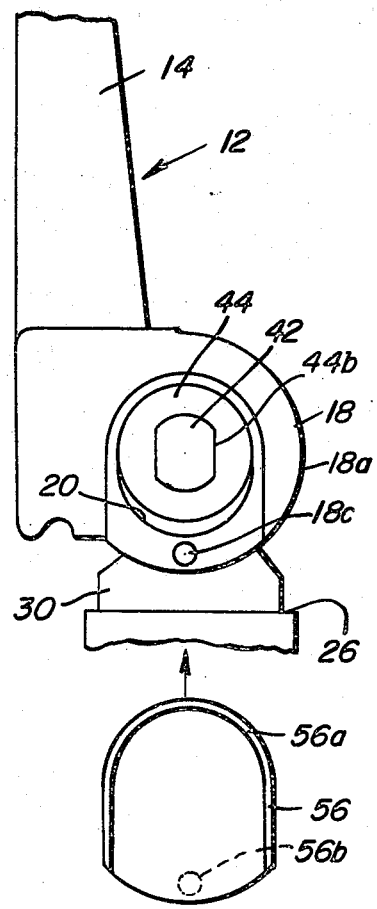
FIG. 6 is an elevational view showing an alternative construction of the embodiment of FIGS. 4 and 5.

Similarly, longitudinal extensibility of the joint can be provided as shown in FIG. 6 by elongating the bore 20 in the condyloid elements longitudinally in the direction of the tibial prosthesis which is the side of bore 20 which is normally not loaded when the joint is weight-bearing. Prior to implanting the device of this invention, bearing blocks 30 are press-fitted into their respective housings. Bearing sleeves 44 are preferably fitted into openings 20 of condyloid elements 18. Femoral prosthesis 12 and tibial prosthesis 22 are then implanted in the femur and tibia, respectively, by cementing fixation shanks 14 and 26 into openings provided in the respective bones. Upstanding arm 36 of weight-bearing portion 24 of tibial prosthesis 22 is then placed between condyloid elements 18 with hole 38 in arm 36 axially aligned with bores 20 in condyloid elements 18. Shaft 42 is then inserted into place and locked into position by pin 48 which is retained by screw 52. Thereafter, end caps 56 are placed in position further locking shaft 42 against transverse movement.

As assembled, outer bearing portions 18a of condyloid elements 18 bear against bearing blocks 30. In like manner, bearing sleeves 44 bear against inner bearing surfaces 18b on condyloid elements 18. In other words, the relative rotational movement which occurs during flexing of the knee occurs at the outer and inner bearing surfaces 18a and 18b, respectively, of condyloid elements 18.

Accordingly, in the construction shown, wear will occur in bearing members 30 and on bearing sleeves 44. There will be little or no wear on outer and inner bearing portions 18a and 18b which are all on the mechanically integral condyloid elements 18. Therefore, the surface worn on sleeve 44 will be concentric with inner bearing 18b, which is concentric with outer bearing 18a, and the surface worn in bearing member 30 will be concentric with bearing 18a. Therefore, even though substantial amounts of plastic bearing materials at 30a and 44 wear away so that the joint components move together and sleeve 44 becomes eccentric to opening 20, the two bearing areas at 18b and 18a remain concentric and true because they are on one single element which was initially made concentric and which undergoes negligible wear in actual use.

In this regard, it should be understood that the words "bearing" and "bear" refer to areas of the prosthesis which support weight or are subjected to force and which experience relative motion. With this arrangement, the deficiencies in the prior art are overcome, and the prosthesis functions smoothly and efficiently over extended periods to closely approximate the anatomical function of the knee or other articulated joint which the prosthesis replaces.

There has above been described a specific embodiment of the present invention. It should be noted, however, that the above embodiment was given for illustrative purposes only and that many alterations and modifications can be practiced by those skilled in the art without departing from the spirit or scope of the present invention. Accordingly, it is the intent that the present invention not be limited to the embodiment illustrated, but only as defined in the appended claims.

I claim:

1. A prosthetic device for joining a pair of human or animal bones having a concentric bearing system which retains its concentricity with wear comprising:
   a first prothesis having a condylar portion and a fixation portion, said condylar portion including two laterally spaced apart condyloid elements each having a first bearing surface defined by the outer periphery of said element and a second bearing surface defined by an opening in said element adapted to receive a transverse support shaft, said fixation portion being adapted to be fixed to one of said bones, said first and second bearing surfaces being concentric and part of the same unitary mechanical element and being adapted to support weight or be subjected to force while experiencing relative motion;
   a second prosthesis having a weight-bearing portion and a fixation portion, said weight-bearing portion including mating bearing surfaces against which said first bearing surfaces of said elements of said first prosthesis bear, said weight-bearing portion having a center portion fitted between the condyloid elements of said first prosthesis, said center portion having an opening adapted to receive a transverse support shaft, said fixation portion being adapted to be fixed to the other one of said bones; and
   a transverse support shaft having a central portion positioned in said opening in said center portion of said second prosthesis and end portions received in said openings in said condyloid elements in said first prosthesis, said shaft being non-rotatably mounted relative to said second prosthesis, said end portions of said shaft being adapted to rotate in said openings in said condyloid elements while bearing against said second bearing surfaces.

2. The prosthetic device of claim 1 in which said mating bearing surfaces of said second prosthesis are made of the same material as said end portions of said shaft.

3. The prosthetic device of claim 1 in which said first and second bearing surfaces of said first prosthesis are arcuate.

4. The prosthetic device of claim 1 in which said first bearing surface of said first prosthesis extends over more than one-half of its outer periphery.

5. The prosthetic device of claim 1 in which said center portion of said weight-bearing portion of said second prosthesis includes means closing said opening to prevent separation of said first and second prosthesis while said shaft is in position.

6. The prosthetic device of claim 1 in which said ends of said transverse support shaft carry bearing sleeves adapted to rotate therewith and against said second bearing surfaces of said first prosthesis.

7. The prosthetic device of claim 1 and further comprising means for preventing transverse movement of said support shaft after installation.

8. The prosthetic device of claim 7 in which said means for preventing transverse movement comprises a pin passing through said shaft and said center portion of said second prosthesis and being prevented from moving transversely by said center portion.

9. The prosthetic device of claim 1 and further comprising means for allowing relative longitudinal extension of said first prosthesis relative to said second prosthesis.

10. The prosthetic device of claim 9 in which said means for providing relative longitudinal movement comprises an elongated opening in said center portion of said second prosthesis which allows said shaft to move longitudinally relative to said second prosthesis.

11. The prosthetic device of claim 9 in which said means for providing relative longitudinal movement comprises an elongated opening in said condyloid elements which allows said shaft to move longitudinally relative to said first prosthesis.

12. A prosthetic knee having a concentric bearing system which retains its concentricity with wear comprising:
   a femoral prosthesis having a condylar portion and a fixation shank adapted to be fixed to the femur, said condylar portion including two laterally spaced apart condyloid elements, said condyloid elements being generally cylindrical in shape and each having a first bearing surface comprising more than one-half of its outer circumference and a second bearing surface defined by a bore in said condyloid element adapted to receive a transverse support shaft, said first and second bearing surfaces being concentric and part of the same unitary mechanical element and being adapted to support weight or be subjected to force while experiencing relative motion;
   a tibial prosthesis having a weight-bearing portion and a fixation shank adapted to be fixed to the tibia, said weight-bearing portion including cylindrical concave bearing surfaces against which said first bearing surfaces of said condyloid elements of said femoral prosthesis bear, said weight-bearing portion having an upstanding arm fitted between the condyloid element of said femoral prosthesis, said upstanding arm having a hole adapted to receive a transverse support shaft;

and a transverse support shaft having a central portion positioned in said hole in said upstanding arm of said tibial prosthesis and end portions carrying bearing sleeves received in said openings in said condyloid elements in said femoral prosthesis, said shaft being non-rotatably mounted relative to said tibial prosthesis, said end portions of said shaft and said bearing sleeves being adapted to rotate in said bores in said condyloid elements while bearing against said second bearing surfaces.

* * * * *